United States Patent
Yang et al.

(10) Patent No.: US 10,376,485 B2
(45) Date of Patent: Aug. 13, 2019

(54) METABOLIC SYNDROME AMELIORATING AGENT

(75) Inventors: Zhi-hong Yang, Tokyo (JP); Hiroko Miyahara, Tokyo (JP); Shuhei Takemura, Tokyo (JP); Akimasa Hatanaka, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 1145 days.

(21) Appl. No.: 14/002,809

(22) PCT Filed: Feb. 29, 2012

(86) PCT No.: PCT/JP2012/055088
§ 371 (c)(1),
(2), (4) Date: Nov. 13, 2013

(87) PCT Pub. No.: WO2012/121080
PCT Pub. Date: Sep. 13, 2012

(65) Prior Publication Data
US 2014/0066508 A1 Mar. 6, 2014

(30) Foreign Application Priority Data

Mar. 4, 2011 (JP) ................................. 2011-047313
May 17, 2011 (JP) ................................. 2011-110227
Sep. 20, 2011 (JP) ................................. 2011-205318

(51) Int. Cl.
*A61K 31/201* (2006.01)
*A61K 31/231* (2006.01)
*A23L 33/115* (2016.01)
*A61K 35/60* (2006.01)

(52) U.S. Cl.
CPC .......... *A61K 31/201* (2013.01); *A23L 33/115* (2016.08); *A61K 31/231* (2013.01); *A61K 35/60* (2013.01)

(58) Field of Classification Search
CPC .... A61K 31/201; A61K 31/231; A61K 35/60; A23L 33/115
See application file for complete search history.

(56) References Cited

FOREIGN PATENT DOCUMENTS

| | | |
|---|---|---|
| JP | 2001-294525 A | 10/2001 |
| WO | 2000056329 A1 | 9/2000 |

OTHER PUBLICATIONS

Gadoleic, 2015, https://en.wikipedia.org/wiki/Gadoleic_acid.*
Neschen et al., 2006, http://www.ncbi.nlm.nih.gov/pubmed/16567512.*
P. Flachs et al. "Polyunsaturated fatty acids of marine origin induce adiponectin in mice fed a high-fat diet", Diabetologia, 2006, vol. 19, pp. 394-397.
Lindqvist, H. et al, "Influence of herring (*Clupea harengus*) and herring fractions on metabolic status in rats fed a high energy diet", Acta Physiologica, 2009, vol. 196, No. 3, pp. 303-314.
T. Mori et al., "Dietary fish oil upregulates intestinal lipid metabolism and reduces body weight gain in C57BL/6J mice", The Joural of Nutrition, 2007, vol. 137, pp. 2629-2634.
T. Ota et al, "Changes in lipids of young and adult saury *Cololabis saira* (pisces)", Marine Ecology Progress Series, 1980, vol. 3, pp. 11-17.
Extended European Search Report for the international patent application No. 12755438.4-1453, dated Jul. 14, 2014.
Yang, Zhi-Hong, et al "Dietary Saury Oil Reduces Hyperglycemia and Hyperlipidemia in Diabetic KKAy Mice and in Diet-Induced Obese C57BL/6J Mice by Altering Gene Expression" LIPIDS, vol. 46, No. 5, Apr. 5, 2011, pp. 425-434.

\* cited by examiner

*Primary Examiner* — Sun Jae Yoo
(74) *Attorney, Agent, or Firm* — Cantor Colburn LLP (57) ABSTRACT

A method for ameliorating metabolic syndrome may include administering, to a patient in need thereof, an effective amount of a monounsaturated fatty acid having 22 carbons or a salt or an ester thereof and/or an effective amount of a monounsaturated fatty acid having 20 carbons or a salt or an ester thereof.

10 Claims, 4 Drawing Sheets

METABOLIC SYNDROME AMELIORATING AGENT

This is the U.S. national stage of application No. PCT/JP2012/055088, filed on 29 Feb. 2012. Priority under 35 U.S.C. § 119(a) and 35 U.S.C. § 365(b) is claimed from Japanese Application No. 2011-047313, filed 4 Mar. 2011, Japanese Application No. 2011-110227 filed 17 May 2011, and Japanese Application No. 2011-205318 filed 20 Sep. 2011, the disclosures of which are also incorporated herein by reference.

TECHNICAL FIELD

The present invention relates to a metabolic syndrome ameliorating agent. More specifically, the present invention relates to a metabolic syndrome ameliorating agent comprising a highly safe food-derived component as an effective component.

BACKGROUND OF INVENTION

In recent years, lifestyle-related diseases have become a problem. Among these, particular attention has been focused on metabolic syndrome. One of the causes of metabolic syndrome is the accumulation of visceral fat. In Japan, a number of diagnostic standards have been announced for metabolic syndrome.

In accordance with one of these standards, if a person has two or more of the symptoms listed below, there is a strong suspicion of metabolic syndrome:

Individuals with visceral fat-type obesity, specifically males with abdominal girth of 85 cm or more, and females with abdominal girth of 90 cm or more; and Systolic blood pressure of 130 mmHg or more, or diastolic blood pressure of 85 mmHg or more, Blood glucose of 100 mg/dL or more on an empty stomach, and Blood neutral lipid value of 150 mg/dL or more, or HDL cholesterol of less than 40 mg/dL.

In addition, cases corresponding to any one of the symptoms above are defined as belonging to the potential metabolic syndrome group.

Previously, the method for treatment and amelioration of metabolic syndrome consisted mainly of food restrictions and exercise treatment. In addition, drugs for individual treatment of the above symptoms have been used as drugs for treatment and amelioration of metabolic syndrome. For example, diabetic treatment drugs, antihypertensive drugs, and antihyperlipidemia drugs, as well as other drugs that lessen white adipose tissue, blood glucose values, blood insulin concentrations, blood cholesterol, blood LDL cholesterol, and blood free fatty acid concentrations, have been used for treatment and amelioration of metabolic syndrome.

In such a circumstance, the development of new ameliorating agents and foods that are effective against the symptoms of metabolic syndrome is strongly desired. In particular, attention is being focused on the efficacy of food and other naturally derived constituents, and an ameliorating agent derived from natural substances is desired.

Fish oil is known to have various effects on the body. Research on efficacy on the body has been performed on some of Omega-3 polyunsaturated fatty acids (n-3 PUFAs). In particular, eicosapentaenoic acid (hereafter called "EPA") and docosahexaenoic acid (hereafter called "DHA") in fish oil are reported to have such effects as prevention of arteriosclerosis, prevention of heart disease, reduction of neutral lipids, prevention of hypertension, amelioration of diabetes, etc.

For example, in Non-patent Document 1, it was reported that n-3 PUFAs such as EPA and DHA improve lipid metabolism, and suppress increases in body weight.

In addition, in Non-patent Document 2, it was reported that n-3 PUFAs such as EPA and DHA induce the expression of adiponectin in adipose cells, to boost the plasma adiponectin levels.

In regard to fatty acid composition, it is known that the characteristic fatty acid composition in fish oil will vary depending on the type of fish. For example, saury, Alaska pollock, capelin, herring, and other offshore swimming fish are, in addition to long-chain n-3 PUFAs, also rich in long-chain monounsaturated fatty acids (MUFAs).

In regard to long-chain MUFAs, it was disclosed in animal experiments and human trials that monoenoic acids having 20 carbons and monoenoic acids having 22 carbons have a reducing action on blood glucose values (Patent Document 1). However, aside from the reducing action on blood glucose values, the physiological action of long-chain MUFAs has not been studied.

In addition, in regard to PUFAs and long-chain MUFAs, the physiological actions of these fatty acids are generally known to show different efficacy depending on the carbon number, as well as the number and positions of double bonds. Regarding the many fatty acids with differing carbon numbers, as well as the number and positions of double bonds, there are a large number of fatty acids remaining for which the physiological actions have not yet been studied. As a result, there is a possibility of further physiological actions existing for PUFAs and long-chain MUFAs, and the discovery of new physiological actions is desired.

CITATION LIST

Patent Documents

Patent Document 1: Japanese Unexamined Patent Application Publication No. 2001-294525

Non-Patent Documents

Non-patent Document 1: Mori T, Kondo H, Hase T, Tokimitsu I, Murase T (2007) Dietary fish oil upregulates intestinal lipid metabolism and reduces body weight gain in C57BL/6J mice. J Nutr 137:2629-2634

Non-patent Document 2: Flachs P, Mohamed-Ali V, Horakova O, Rossmeisl M, Hosseinzadeh-Attar M J, Hensler M, Ruzickova J, Kopecky J (2006) Polyunsaturated fatty acids of marine origin induce adiponectin in mice fed a high-fat diet. Diabetologia 49:394-397

SUMMARY OF INVENTION

Technical Problem

In view of the above, an object of the present invention is to provide an ameliorating agent for improving metabolic syndrome.

Solution to Problem

As mentioned above, it is known that the double bonding in fatty acids, if differing in position and number, can vary in efficacy in regard to the body. In addition, it is known that the carbon number in fatty acids, if differing in length, can vary in efficacy in regard to the body. The inventors of the present invention focused on the physiological actions and efficacy of MUFAs richly contained in saury oil or Alaska pollock oil and, as a result of repeated research, discovered that MUFA having 20 carbons (hereafter expressed as C20:1) and MUFA having 22 carbons (hereafter expressed as C22:1) have an ameliorative effect on metabolic syndrome, and achieved the present invention.

The present invention provides a metabolic syndrome ameliorating agent comprising: a MUFA having 22 carbons or a salt or an ester thereof and/or a MUFA having 20 carbons or a salt or an ester thereof, as an effective component.

In addition, the present invention provides the abovementioned metabolic syndrome ameliorating agent, wherein the ester of the MUFA having 22 carbons and/or the MUFA having 20 carbons is a glyceride.

In addition, the present invention provides the abovementioned metabolic syndrome ameliorating agent, wherein the glyceride of the MUFA having 22 carbons and/or the MUFA having 20 carbons is a fish oil.

In addition, the present invention provides the abovementioned metabolic syndrome ameliorating agent, wherein a proportion of the MUFA having 22 carbons and the MUFA having 20 carbons to the total fatty acids is greater than or equal to 30% by weight, greater than or equal to 40% by weight, or greater than or equal to 50% by weight.

Furthermore, the present invention provides a food product which is labeled for use as a metabolic syndrome ameliorant, the food product comprising: a MUFA having 22 carbons or a salt or an ester thereof and/or a MUFA having 20 carbons or a salt or an ester thereof.

Advantageous Effects of Invention

The metabolic syndrome ameliorating agent in the present invention can treat and improve many of the symptoms of metabolic syndrome. In particular, the metabolic syndrome ameliorating agent in the present invention can decrease white adipose tissue, blood glucose values, blood insulin concentrations, blood cholesterol, blood LDL cholesterol, and blood free fatty acid concentrations. In addition, the metabolic syndrome ameliorating agent in the present invention can suppress the expression of fatty acid synthesis genes in adipose tissue. Furthermore, the metabolic syndrome ameliorating agent in the present invention can promote the expression of energy metabolism genes.

INDUSTRIAL APPLICABILITY

Medical drugs or food products comprising the MUFA having 22 carbons and/or MUFA having 20 carbons of the present invention can be provided for prevention or amelioration of metabolic syndrome.

DESCRIPTION OF EMBODIMENTS

Here follows a description of the metabolic syndrome ameliorating agent in the present invention. The metabolic syndrome ameliorating agent in the present invention is a C22:1 and/or C20:1, or a salt, or ester comprising these as constituent fatty acids. The metabolic syndrome ameliorating agent also includes oils derived from natural materials such as oils of marine products and microorganisms containing these C22:1 and/or C20:1, or the salt or the ester.

Any raw material or form can be used as the C22:1 and/or C20:1 used in the metabolic syndrome ameliorating agent in the present invention only if it is allowed to use for medical drugs and food products. For example, fish oil such as a saury oil can be used either as is or refined. In addition, oils derived from seals and whales or other animals can also be used. Furthermore, even raw materials that do not contain much MUFA can be used by concentrating the MUFA.

Saury raw fish oil is normally obtained by the same method as other fish oils, as described below. The fish heads, skin, bones, viscera, and other processing residue, generated from the whole body of the saury or from marine processing, is crushed and steamed, and then compressed and separated into a broth (stickwater, SW) and compressed meal. The oils obtained in the broth are separated in a centrifuge from the broth.

The 5th Revision of the Standard Tables of Food Composition in Japan shows that docosenoic acid (C22:1) incorporated in the saury (raw) fatty acid at 19.3% by weight, icosenoic acid (C20:1) at 17.2% by weight, and the total weight of MUFA at 50.1% by weight. A characteristic of saury oil is the large amount of MUFA content among fish oils.

In general, the crude oil from fish oil is passed through degumming, deacidifying, decoloring, and deodorizing processes, etc., to obtain refined fish oil. This refined fish oil can be used as a MUFA supply source. In addition, if using oil with boosted concentrations of MUFA, concentrating methods using lipase reactions, or methods involving concentration of MUFA ethyl esters after ethyl esterification, followed by an ester exchange between glycerine and ethyl ester and reformulation into triglycerides can be used to obtain triglycerides enriched with MUFA.

In addition, the MUFA used in the metabolic syndrome ameliorating agent in the present invention can also be a salt or ester comprising these. Possible examples for salt are potassium salt and sodium salt. In addition, possible examples for esters are a lower alcohol ester with carbon number of 5 or less, esters with glycerine such as monoglyceride, diglyceride and triglyceride, as well as phospholipids. Most desirable are glycerine esters, ethyl esters, or the like.

In addition, for the MUFA used in the metabolic syndrome ameliorating agent in the present invention, fish oil comprising a C22:1 glyceride and/or a C20:1 glyceride can be used. C22:1 and C20:1 can vary in content depending on the fish type, and fish types with a large content include fish of the family Scomberesocidae such as saury; fish of the family Gadidae, such as Pacific cod, Alaska pollock, Atlantic pollock, and sablefish; fish of the family Salmonidae, such as chum salmon, coho salmon, sockeye salmon, pink salmon, Atlantic salmon, and rainbow trout; fish of the family Osmeridae, such as Karafuto capelin, and capelin; fish of the family Clupeidae, such as herring. Other fish with relatively high levels include sand eel, tuna, mackerel, and red bream. In addition, the liver oil from northern dogfish, basking sharks, silver chimaera, and other sharks also contain large amounts. It is desirable that fish oil refined from these fish be used in the ameliorating agent in the present invention.

In this Specification, metabolic syndrome refers to metabolic syndrome in its broadest possible meaning. For example, while metabolic syndrome comprises symptoms based on the diagnostic standards below, other symptoms on other voluntary diagnostic standards are also not excluded:

Individuals with visceral fat-type obesity, specifically males with abdominal girth of 85 cm or more, and females with abdominal girth of 90 cm or more; and Systolic blood pressure of 130 mmHg or more, or diastolic blood pressure of 85 mmHg or more, Blood glucose of 100 mg/dL or more on an empty stomach, and Blood neutral lipid value of 150 mg/dL or more, or HDL cholesterol of less than 40 mg/dL.

In addition, cases corresponding to any one of the symptoms above are defined as belonging to the potential metabolic syndrome group, and symptoms in the potential metabolic syndrome group are also included in metabolic syndrome.

Metabolic syndrome amelioration refers to improvement of symptoms for metabolic syndrome patients and for any symptoms diagnosed as the potential metabolic syndrome group. For example, reduced white adipose tissue, blood glucose values, blood insulin concentrations, blood cholesterol, blood LDL cholesterol, and blood free fatty acid concentrations, are included. In addition, metabolic syndrome amelioration comprises raising blood adiponectin concentrations, lessening adipocytokine resistin and TNF-α concentrations, improving insulin tolerance, suppressing expression of SCD-1 (stearoyl CoA desaturase-1), which is a fatty acid synthesis system gene in adipose tissue, and lessening the amount of visceral fat.

The metabolic syndrome ameliorating agent in the present invention can also, in addition to the abovementioned C22:1 and C20:1, be a composition comprising optional constituents. For example, the metabolic syndrome ameliorating agent in the present invention can, when used as a medical drug, be provided as a composition together with pharmaceutically acceptable bases, carriers, excipients, disintegrators, lubricants, colorants, and the like. Preferably, since it is a liquefied oil, it is recommended that the metabolic syndrome ameliorating agent be processed together with gelatin or other soft capsules, and powdered oils, so that it can be provided as a pill or capsule.

Aside from the above, the metabolic syndrome ameliorating agent in the present invention be provided as a food product comprising C22:1, C20:1, and/or fish oil. In the present invention, food product means food products in general, including beverages, and comprises ordinary food products that include supplements and other health food products, as well as food for specified health uses and food with nutrient function claims as regulated in the Food for Special Dietary Uses standard of the Consumer Affairs Agency of Japan. For example, functional food products labeled for use as a metabolic syndrome ameliorant are provided. For example, food products comprising fish oil can be provided as is. In addition, it can be added to, mixed with, or coated onto, other food products, etc., to provide food products that confer a metabolic syndrome ameliorative effect as a food product constituent. Aside from food products, it can also be provided as feed for animals, or the like.

In addition, food products comprising C22:1, C20:1, and/or fish oil can be provided as products packaged together with explanatory manuals describing that the food product is for use as a metabolic syndrome ameliorant.

The metabolic syndrome ameliorating agent in the present invention can include C22:1, C20:1, and/or fish oil in volumes necessary for inducing a metabolic syndrome amelioration action. The metabolic syndrome ameliorating agent in the present invention can, when administered to patients as a medical drug or food product, be administered without restriction in accordance with such requirements as the degree of symptoms, or the patient's age, body weight, and health conditions, etc., but, if the patient is an adult, the C22:1, C20:1, and/or fish oil can be administered either orally or non-orally at appropriate intervals once per day or divided into 2 to 4 times per day or more, at 1 mg to 1 g/kg/day, and preferably at 5 mg to 300 mg/kg/day. In addition, since the metabolic syndrome ameliorating agent in the present invention does not have any of the powerful effects or side-effects of medical drugs, there is no limit to the ingestion volume per day.

Working Example 1

(Materials and Methods)

As saury oil comprising C22:1 and C20:1, purified saury oil was used, which is obtained by decoloring the saury crude oil using a silica gel and activated clay, and then deodorized the oil using steam distillation. Soybean oil was obtained from Oriental Yeast Co., Ltd., and lard from Camellia Co., Ltd. The respective fatty acid compositions of the oils and fats are shown in Table 1.

TABLE 1

Fatty Acid Composition of Soybean Oil, Lard, and Saury Oil (%)

| Fatty acid (g/100 g fatty acid) | Soybean oil | Lard | Saury oil |
| --- | --- | --- | --- |
| C14:0 | 0.06 | 1.49 | 5.68 |
| C16:0 | 9.49 | 25.43 | 9.23 |
| C16:0 | 0.10 | 2.35 | 2.99 |
| C18:0 | 3.86 | 5.97 | 1.66 |
| C18:1 | 22.8 | 40.64 | 5.83 |
| C18:2 n-6 | 55.14 | 10.81 | 1.60 |
| C18:3 n-3 | 7.55 | 1.00 | 1.22 |
| C20:0 | 0.33 | 0.21 | 0.19 |
| C20:1 n-9, n-7 | 0.20 | 0.80 | 15.24 |
| C20:4 n-6 | ND | 0.20 | 0.63 |
| C20:5 n-3 | ND | 0.02 | 6.11 |
| C22:1 n-11, n-9 | 0.05 | ND | 19.51 |
| C22:5 n-3 | 0.00 | 0.10 | 1.56 |
| C22:6 n-3 | ND | 0.03 | 11.82 |

The values in the table are based on averages of measured values of three separate samples measured independently. In addition, in the table, ND indicates "no detection".

Preparing of MUFA-concentrated saury oil was performed as shown below. Saury oil was subjected to ethyl esterification and applied to the ODS column, and MUFA ethyl ester fractions are separated. Then, an enzyme lipase was used to perform ester exchange between glycerine and the ethyl ester, and reformulate into triglycerides. As a result of analysis of this saury MUFA oil, the lipid composition was found to be 100% triglycerides, and the fatty acid composition is shown in Table 2.

TABLE 2

Fatty Acid Composition of Lard and MUFA-Concentrated Saury Oil

| Fatty acid (g/100 g fatty acid) | Lard | MUFA |
|---|---|---|
| C14:0 | 1.49 | 0.34 |
| C14:1 | 0.05 | 0.03 |
| C16:0 | 25.43 | 8.17 |
| C16:1 | 2.35 | 0.33 |
| C18:0 | 15.97 | 3.55 |
| C18:1n-9 | 40.64 | 1.59 |
| C18:1n-7 | ND | 2.57 |
| C18:2n-6 | 10.81 | 0.17 |
| C18:3n-6 | 0.07 | 0.08 |
| C18:3n-3 | 1.00 | 0.03 |
| C20:0 | 0.21 | 0.36 |
| C20:1n-9 | 0.80 | 22.78 |
| C20:1n-7 | ND | 5.44 |
| C20:4n-6 | 0.20 | 0.31 |
| C20:4n-3 | ND | 1.08 |
| C20:5n-3 | 0.02 | 0.12 |
| C22:1 n-11 | ND | 38.98 |
| C22:1n-9 | ND | 2.47 |
| C22:5n-3 | 0.10 | 0.09 |
| C22:6n-3 | 0.03 | 1.22 |

In the table, ND indicates "no detection".

Spontaneously diabetic KKAy mice were obtained from CLEA Japan, Inc. C57BL/6J mice were obtained from Charles River Laboratories Japan, Inc.

(Insulin Tolerance Test, and Measurement of Plasma Glucose)

For the insulin tolerance test, after five hours of fasting, an insulin aqueous solution of 0.75 U/kg was administered intraperitoneally. In addition, immediately before the insulin administration (0 minutes), and also 20 minutes, 40 minutes, 60 minutes, and 80 minutes after administration, retroorbital blood sampling was performed, and Glucose CII-Test Wako was used to measure blood glucose values.

(Measurement of Adiponectin, Resistin, TNF-α, and Leptin Plasma Concentrations)

For the adiponectin, resistin, TNF-α, and leptin concentrations in blood, the Mouse Adiponectin ELISA Kit (Otsuka Pharmaceutical Co., Ltd.), Mouse Resistin ELISA Kit (Shibayagi Co., Ltd.), Mouse TNF-α ELISA Kit (Shibayagi Co., Ltd.), and Mouse Leptin ELISA Kit (Morinaga Institute of Biological Science, Inc.) were used to perform the respective measurements.

(Measurement of Blood Total Cholesterol Concentrations, Blood HDL Cholesterol Concentrations, Blood Triglyceride Concentrations, and Blood Insulin Concentrations)

For the blood total cholesterol concentrations, blood HDL cholesterol concentrations, and blood triglyceride concentrations, the Cholesterol E Test Wako (Wako Pure Chemical Industries, Ltd.), HDL Cholesterol Test Wako (Wako Pure Chemical Industries, Ltd.), and Triglyceride E Test Wako (Wako Pure Chemical Industries, Ltd.) were used to perform the respective measurements. For the blood insulin concentrations, the Morinaga Insulin Measurement Kit (Morinaga Institute of Biological Science, Inc.) was used to perform measurements.

(mRNA Measurement)

For mRNA measurement, cDNA synthesized using total RNA extracted from intestinal membrane white adipose tissue was used, through performance of a real-time PCR reaction, to evaluate the amount of expression of genes related to lipid metabolism. An 18s ribosome RNA gene was used as an endogenous contrasting gene. With the amount of gene expression in the control group set to 1, the relative expression amount for each gene in the saury oil administration group was calculated. The primer in each gene is as shown below.

TABLE 3

| Gene | Primer Sequence | Accession Number |
|---|---|---|
| SREBP-1c | 5'-GATGTGCGAACTGGACACAG-3'<br>5'-CATAGGGGGCGTCAAACAG-3' | NM_011480 |
| SCD-1 | 5'-TTCTTGCGATACACTCTGGTGC-3'<br>5'-CGGGATTGAATGTTCTTGTCGT-3' | NM_009127 |
| FAS | 5'-GGAGGTGGTGATAGCCGGTAT-3'<br>5'-TGGGTAATCCATAGAGCCCAG-3' | NM_007988 |
| ACC | 5'-ATGGGCGGAATGGTCTCTTTC-3'<br>5'-TGGGGACCTTGTCTTCATCAT-3' | NM_133360 |
| CPT-1 | 5'-CTCCGCCTGAGCCATGAAG-3'<br>5'-CACCAGTGATGATGCCATTCT-3' | NM_013495 |
| PGC-1 α | 5'-GAAGTGGTGTAGCGACCAATC-3'<br>5'-AATGAGGGCAATCCGTCTTCA-3' | NM_008904 |
| PGC-1 β | 5'-TCCTGTAAAAGCCCGGAGTAT-3'<br>5'-GCTCTGGTAGGGGCAGTGA-3' | NM_133249 |

Test 1 (Saury Oil Efficacy for Metabolic Syndrome in Spontaneously Diabetic KKAy Mice)

For the spontaneously diabetic KKAy mice (n=10), a feed mix with soybean oil 10% (control group) or a feed mix with saury oil 10% (shown in Table 4) was administered in four weeks of pair feedings. The 4-week average feed volume was 4.44 g/day. After the mixed feed period was completed, the saury oil administration group and control group were compared.

Test 2 (Saury Oil Efficacy for Metabolic Syndrome in Feed-Induced Obese Mice C57BL/6J)

For the feed-induced obese mice C57BL/6J, a lard of 32% mixed high-fat feed (control group), or a lard 22%+saury oil 10% mixed high-fat feed was administered for a mixed feed period of 6 weeks (shown in Table 4). The 6-week average feed volume for the control group was 2.49 g/day, and for the saury oil group, 2.68 g/day. After the mixed feed period was completed, the saury oil administration group and control group were compared.

TABLE 4

Compositions (%) of feed used in 4-week feeding test for KKAy mice and 6-week feeding test for C57BL/6J mice

|  | KKAy mice | | C57BL/6J mice | |
|---|---|---|---|---|
|  | Soybean oil feed | Saury oil feed | Lard feed | Saury oil feed |
| Casein | 20 | 20 | 25.8 | 25.8 |
| L-cystine | 0.3 | 0.3 | 0.4 | 0.4 |
| Corn starch | 49.9 | 49.9 | — | — |
| Maltodextrin 10 | — | — | 16.2 | 16.2 |
| Sucrose | 10 | 10 | 8.9 | 8.9 |
| Cellulose | 5 | 5 | 6.5 | 6.5 |
| Mineral mixture | 3.5 | 3.5 | 1.3 | 1.3 |
| Vitamin mixture | 1 | 1 | 1.3 | 1.3 |
| Choline bitartrate | 0.3 | 0.3 | 0.3 | 0.3 |
| Soybean oil | 10 | — | 3.2 | 3.2 |
| Lard | — | — | 32 | 22 |
| Saury oil | — | 10 | — | 10 |

(Results)

Table 5 shows the efficacy of saury oil for the mouse weight, mesenteric WAT mass, plasma markers of glucose and lipid metabolism in both tests.

TABLE 5

Efficacy of Saury Oil for Mouse Weight, Mesenteric WAT Mass, and Plasma Markers of Glucose and Lipid Metabolism in KKAy Mice and Feed-Induced Obese C57BL/6J Mice

|  | KKAy mice | | C57BL/6J mice | |
| --- | --- | --- | --- | --- |
|  | Soybean feed (Control) | Saury oil feed | Lard feed (Control) | Saury oil feed |
| Weight (g) | 36.9 ± 0.6 | 37.9 ± 0.4 | 31.6 ± 1.3 | 32.1 ± 2.1 |
| WAT mass (g) | 2.4 ± 0.1 | 2.17 ± 0.1 * | 1.7 ± 0.09 | 1.7 ± 0.13 |
| Glucose (mg/dl) | 541.5 ± 20.1 | 467.3 ± 8.2 * | 301.4 ± 11.2 | 258.9 ± 19.8* |
| Insulin (ng/ml) | 40.9 ± 4.4 | 22.3 ± 2.3 ** | 4.7 ± 0.6 | 3.1 ± 0.4 * |
| TC (mg/dl) | 109.3 ± 3.7 | 65.9 ± 2.6 *** | 134.7 ± 4.2 | 107.2 ± 5.1*** |
| LDL-C (mg/dl) | 45.9 ± 2.4 | 18.5 ± 1.2 *** | 28.2 ± 6.4 | 20.5 ± 3.4 * |
| TAG (mg/dl) | 67.6 ± 9.1 | 54.1 ± 4.6 | 76.6 ± 5 | 60.5 ± 4.9 * |
| NEFA (mEq/l) | 1.1 ± 0.07 | 0.8 ± 0.04 $^b$ | 0.5 ± 0.03 | 0.48 ± 0.06 |

WAT: White adipose tissue, TC: Total cholesterol, LDL-C: Low-density lipoprotein cholesterol, TAG: Triglyceride, NEFA: Non-esterified fatty acid.

As shown in Table 5, the KKAy mice given a mixed feed containing 10% saury oil for four weeks showed significant decrease compared with the control group in all items including white adipose tissue, blood glucose values, blood insulin concentrations, blood cholesterol, blood LDL-cholesterol, and blood free fatty acid concentrations.

For the C57BL/6J mice, as well, the C57BL/6J mice given a mixed feed containing 10% saury oil showed significant decrease of blood glucose values, blood insulin concentrations, blood cholesterol, blood LDL cholesterol, and blood triglyceride concentrations. In addition, the values in the table shows an average±SE. *, , and * indicate a significant difference from the control group of P<0.05, P<0.01, and P<0.001, respectively.

Figure 1:
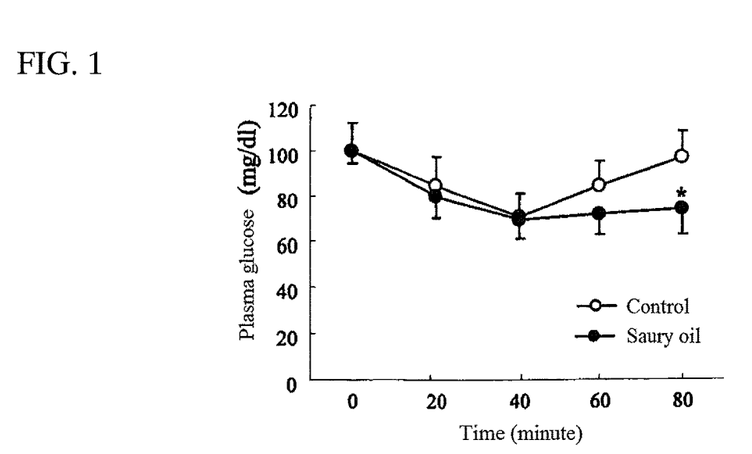
FIG. 1 is a diagram showing efficacy of saury oil on amelioration of insulin sensitivity.

FIG. 1 is a figure showing the efficacy of saury oil on insulin tolerance in the KKAy mice. In the KKAy mice given a mixed feed containing 10% soybean oil (control group) or a mixed feed containing 10% saury oil for three weeks, an insulin tolerance test was performed. The values in the figure have been standardized in relation to the control group. In addition, the values in the figure show an average±SE. * indicates a significant difference from the control group of P<0.05.

As shown in FIG. 1, in the insulin tolerance test, the KKAy mice given a mixed feed containing 10% saury oil for three weeks demonstrated an ameliorative effect in insulin tolerance compared with the KKAy mice given a mixed feed containing 10% soybean oil (control group).

Figure 2:
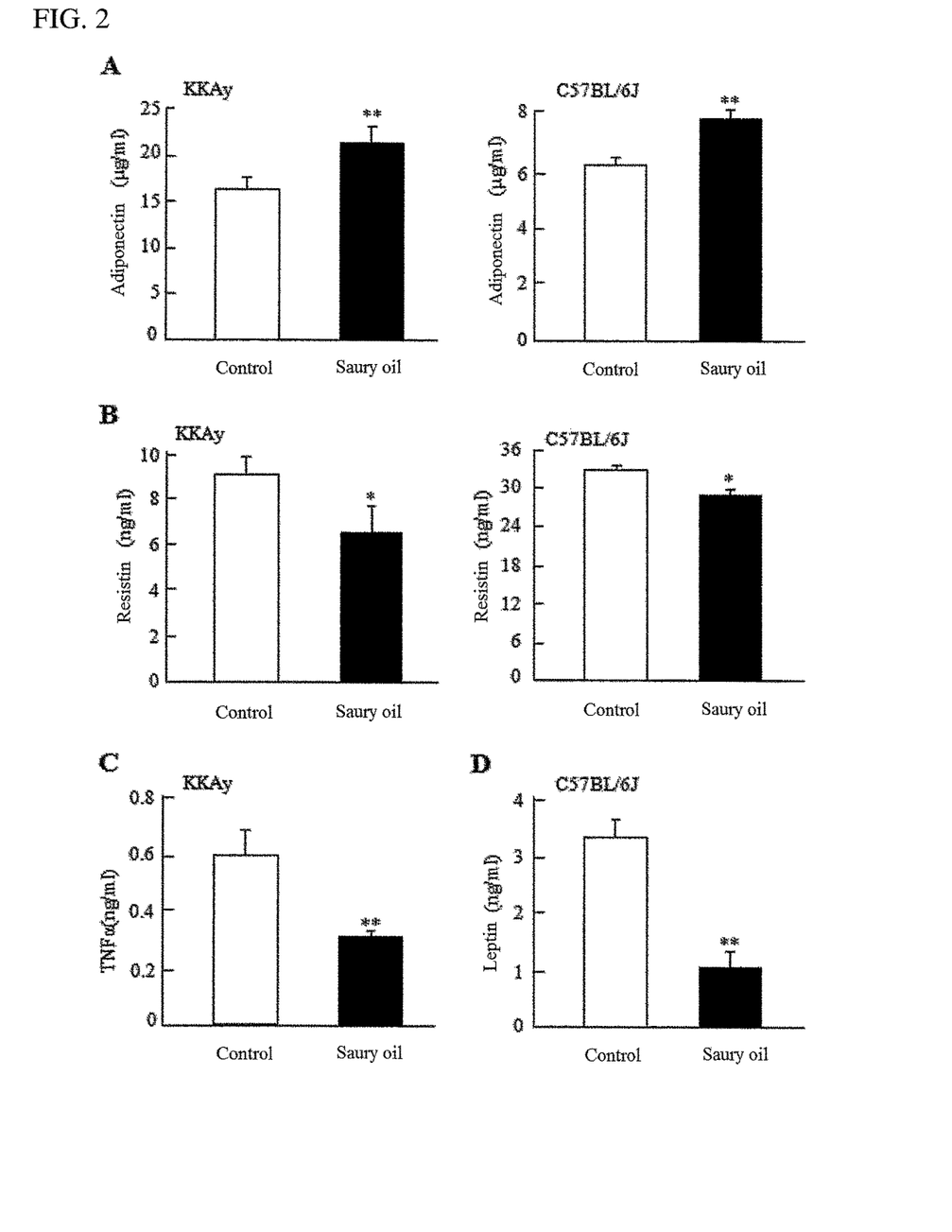
FIGS. 2A to 2D are diagrams showing efficacy of saury oil on plasma adipokines.

FIG. 2A to 2D are figures showing the efficacy of saury oil on plasma protein concentrations that are a benchmark for metabolic syndrome. After the mixed feed period was completed, ELISA was used to measure to the plasma adipokine levels. FIG. 2A shows the plasma adiponectin concentrations in the spontaneously diabetic KKAy mice (left) and the feed-induced obese C57BL/6J mice (right). FIG. 2B shows the plasma resistin concentrations in the KKAy mice (left) and the feed-induced obese C57BL/6J mice (right). FIG. 2C shows the plasma TNF-α concentrations in the KKAy mice. FIG. 2D shows the plasma leptin concentrations in the feed-induced obese C57BL/6J mice. The respective values show an average±SE (n=10). * and ** indicate a significant difference from the control group (*: P<0.05, **: P<0.001).

As shown in FIG. 2A, the KKAy mice given the saury oil showed a significant increase in the blood adiponectin concentrations. On the other hand, the pro-inflammatory adipocytokine resistin and TNF-a concentrations were significantly lower in the KKAy mice given the saury oil (FIGS. 2B and 2C). It was concluded that the feed comprising saury oil was linked to the favorable blood adipokine changes, and to the amelioration of blood glycolipid metabolism and the amelioration of insulin tolerance.

The C57BL/6J mice, as well, given a mixed feed containing 10% saury oil, showed a significant increase in the blood adiponectin concentrations. On the other hand, as shown in FIG. 2B, the pro-inflammatory adipocytokine resistin concentrations were significantly lower in the C57BL/6J mice given a mixed feed containing 10% saury oil. In addition, as shown in FIG. 2D, the blood leptin concentrations were significantly lower in the C57BL/6J mice given a mixed feed containing 10% saury oil. This suggested that use of feed comprising saury oil improved leptin resistance due to obesity. Saury oil was concluded to be linked to favorable blood adipokine changes, and to the amelioration in blood glycolipid metabolism and the amelioration in insulin tolerance.

Figure 4:
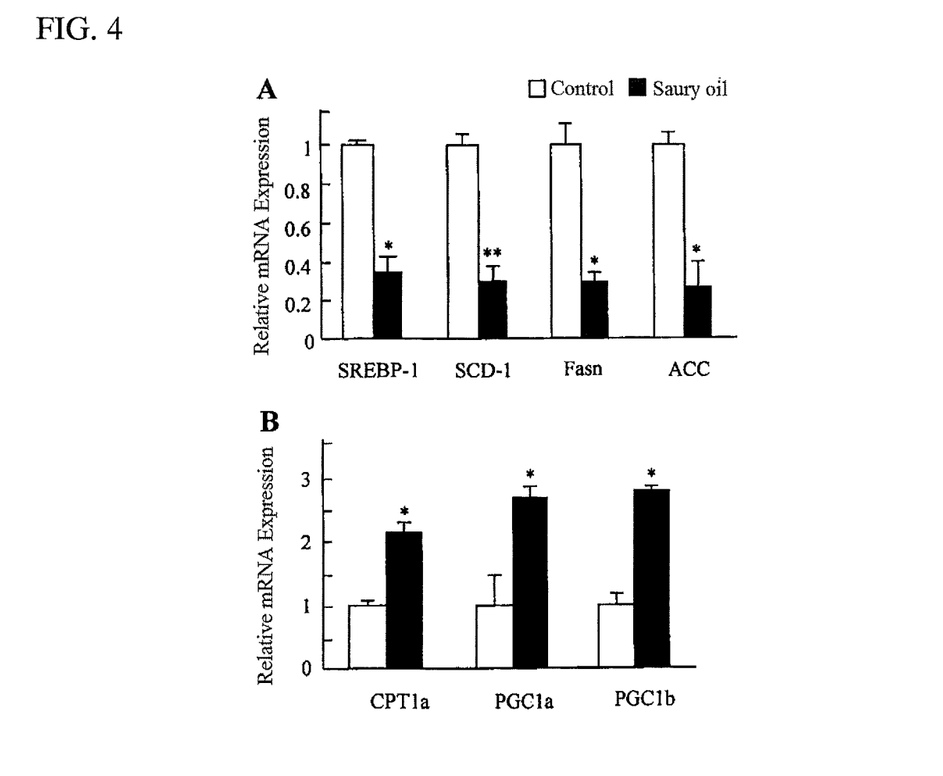
FIGS. 4A and 4B are diagrams showing efficacy of saury oil on expression of genetic mRNA related to lipid metabolism in mesenteric WAT.

After the mixed feed period was completed, mRNA expression of the respective genes in the C57BL/6J mouse mesenteric WAT was measured using real-time PCR. FIGS. 4A and 4B are figures showing efficacy of saury oil on expression of genetic mRNA related to lipid metabolism in mesenteric WAT. FIG. 4A is a figure showing the fatty acid synthesis genes in adipose tissue SREBP-1 (Sterol regulatory element binding protein 1), SCD-1 (Stearoyl CoA desaturase-1), FAS (Fatty acid synthase), and ACC (Acetyl-CoA carboxylase), expression. FIG. 4B is a figure showing the rate limiting enzyme in fatty acid β oxidizing CPT-1 (Carnitine palmitoyltransferase-1) gene, and energy metabolic system gene PGC-1α (Peroxisome proliferator-activated receptor gamma coactivator 1-alpha) and PGC-1β (Peroxisome proliferator-activated receptor gamma coactivator 1-beta) expression. mRNA was standardized in relation to the 18S ribosome RNA, and expressed in relation to the control group. The respective values show an average±SE (n=10). * and ** indicate a significant difference from the control group (*: P<0.05, **: P<0.001).

As shown in FIG. 4A, the C57BL/6J mice given a mixed feed containing 10% saury oil had the SREBP-1, SCD-1, FAS, and ACC expression suppressed. In addition, as shown in FIG. 4B, the C57BL/6J mice given a mixed feed containing 10% saury oil had the CPT-1, PGC-1α, and PGC-1β expression promoted. It was concluded that the long-term administration of saury oil was linked to lessening of the amount of visceral fat and amelioration of insulin tolerance.

Test 3 (Saury Oil Efficacy for Metabolic Syndrome in Spontaneously Diabetic KKAy Mice)

Figure 3:
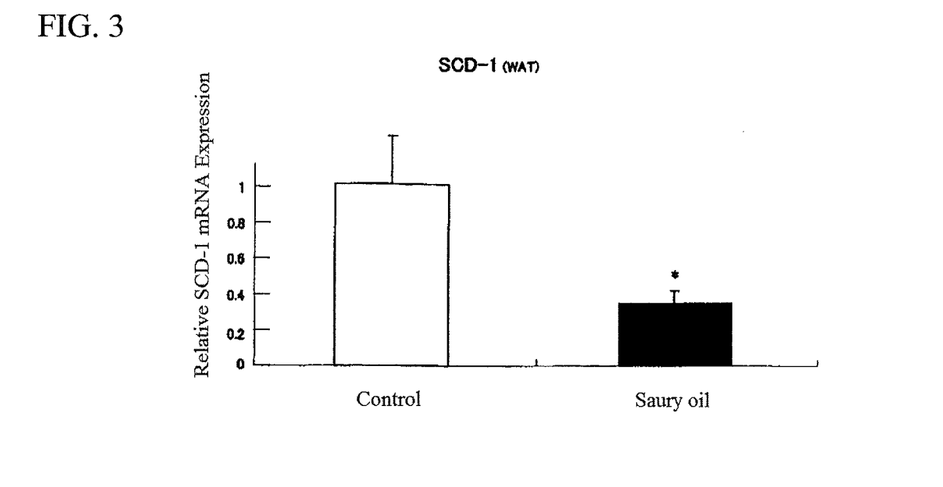
FIG. 3 is a diagram showing efficacy of saury oil on expression of SCD-1 mRNA in mesenteric WAT.

A mixed feed containing 10% soybean oil (control group) or a mixed feed containing 10% saury oil was given to the KKAy mice for six weeks. After the treatment period, SCD-1 mRNA expression in mesenteric WAT was measured using real-time PCR. FIG. 3 is a figure showing efficacy in the KKAy mice of saury oil on expression of SCD-1 mRNA in mesenteric WAT. mRNA was standardized in relation to the 18S ribosome RNA, and expressed in relation to the control group. The value shows an average±SE (n=10). * indicates a significant difference from the control group of p<0.05. As shown in FIG. 3, the KKAy mice given saury oil had the fatty acid synthesis genes in adipose tissue SCD-1 (Stearoyl CoA desaturase-1) expression suppressed. It was concluded that the long-term administration of saury oil was linked to lessening of the amount of visceral fat and amelioration of insulin tolerance.

COMPARATIVE EXAMPLES

The abovementioned tests investigated the efficacy of saury oil on metabolic syndrome amelioration. On the other hand, saury oil also includes some amounts of EPA/DHA. Tables 6 and 7 below show comparisons of the results of tests using these EPA/DHA with our tests using the saury oil.

TABLE 6

|  | Cited Reference 1)* | Our Test |
|---|---|---|
| Test animals | C57BL/6J mice | C57BL/6J mice |
| Control group | 30% TG | 32% Lard |
| Administration period | 5 months | 6 weeks |
| EPA/DHA content in fatty acid composition (%) | 50.7% | 18% |
| Fish oil content in feed (%) | 4% | 10% |
| EPA/DHA content in feed (%) | 2% | 1.8% |
| Blood glucose value | No change | Significantly lowered |
| Blood cholesterol concentration | No change | Significantly lowered |
| Blood triglyceride concentration | No change | Significantly lowered |

Cited Reference 1)* For EPA/DHA fish oil of this concentration, the method of expression in this reference citation is [4% FO].
Mori T, Kordo H, Hase T, Tokimitsu I, Murase T (2007) Dietary fish oil upregulates intestinal lipid metabolism and reduces body weight gain in C57BL/6J mice. J Nutr 137: 2629-2634

TABLE 7

|  | Cited Reference 2)* | Our Test |
|---|---|---|
| Test animals | C57BL/6J mice | C57BL/6J mice |
| Control group | 35% TG | 32% Lard |
| Administration period | 5 weeks | 6 weeks |
| EPA/DHA content in fatty acid composition (%) | 57% | 18% |
| Fish oil content in feed (%) | 15% | 10% |
| EPA/DHA content in feed (%) | 8.55% | 1.8% |
| Blood glucose value | No change | Significantly lowered |
| Blood leptin concentration | No change | Significantly lowered |

Cited Reference 2)* For EPA/DHA fish oil of this concentration, the method of expression in this reference citation is [cGF-F1].
Flachs P, Mohamed-Ali V, Horakova O, Rossmeisl M, Hosseinzadeh-Attar M J, Hensler M, Ruzickova J, Kopecky J (2006) Polyunsaturated fatty acids of marine origin induce adiponectin in mice fed a high-fat diet. Diabetologia 49: 394-397

As shown in Table 6, the test in Cited Reference 1 showed the EPA/DHA content in feed (%) at 2%, and the EPA/DHA content (%) included in the saury oil used in our test this time was less than that, at 1.8%. In the test in Cited Reference 1, while no particular efficacy was shown in regard to the blood glucose values, blood cholesterol concentrations, and blood triglyceride concentrations, however, in our test this time, the respective values were significantly reduced. Therefore, it was concluded that the efficacy of saury oil is not based on the EPA/DHA comprised in the saury oil, but is based on the C22:1 and C20:1 that is contained in large amounts in the saury oil.

In addition, as shown in Table 7, the test in Cited Reference 2 showed the EPA/DHA content in feed (%) at 8.55%, and the EPA/DHA content (%) included in the saury oil used in our test this time was 1.8%, a much lower amount. In the test in Cited Reference 2, while no particular efficacy was shown in regard to the blood glucose values and blood leptin concentrations, however, in our test this time, the respective values were significantly less. Therefore, it was concluded that the efficacy of saury oil is not based on the EPA/DHA comprised in the saury oil, but is based on the C22:1 and C20:1 that is contained in large amounts in the saury oil.

Test 4 (MUFA-Concentrated Saury Oil Efficacy for Metabolic Syndrome in Feed-Induced Obese C57BL/6J Mice)

With consideration for the results of the abovementioned comparative examples, to investigate whether the efficacy of saury oil is based on C22:1 and C20:1 of the saury oil, saury oil enriched with these fatty acids was used to investigate the efficacy on metabolic syndrome.

For the feed-induced obese mice C57BL/6J, a lard 33% mixed high-fat feed (control group), or lard 28%+MUFA-concentrated saury oil 5% mixed high-fat feed was administrated, for a mixed feed period of 6 weeks (shown in Table 8). After feeding, all blood were taken from C57BL/6J mice, and plasma obtained from a centrifuge was used to perform blood biochemical tests as well as comparisons of the MUFA-concentrated saury oil administration group and the control group.

TABLE 8

Composition Analysis of High Fat Feed or High Fat Feed Mixing MUFA, Raising C57BL/6J Mice

| Ingredient (g/100 g diet) | Lard feed (Control group) | MUFA feed |
|---|---|---|
| Casein | 25.8 | 25.8 |
| L-cystine | 0.4 | 0.4 |
| Maltodextrin 10 | 16.2 | 16.2 |
| Sucrose | 8.9 | 8.9 |
| Cellulose | 6.5 | 6.5 |
| Mineral mixture | 1.3 | 1.3 |
| Vitamin mixture | 1.3 | 1.3 |
| Choline bitartrate | 0.3 | 0.3 |
| Soybean oil | 3.2 | 3.2 |
| Lard | 33 | 28 |
| MUFA fraction | — | 5 |

(Results)

Table 9 shows the efficacy of MUFA-concentrated saucy oil for the mouse weight, mesenteric WAT mass, plasma markers of glucose and lipid metabolism in Test 4. The respective values show an average±SE (n=10). The superscripted symbols indicate a significant difference from the control group (*: P<0.05, : P<0.01, *: P<0.001).

TABLE 9

|  | Lard feed (Control group) | MUFA feed |
|---|---|---|
| Weight (g) | 30.9 ± 0.29 | 30.8 ± 0.54 |
| WAT weight (mg) | 163 ± 9.5 | 165 ± 6.1 |
| Glucose (mg/dl) | 366 ± 31.2 | 260.1 ± 7.9** |
| Insulin (ng/ml) | 4.6 ± 0.8 | 2.5 ± 0.4* |

TABLE 9-continued

|  | Lard feed (Control group) | MUFA feed |
|---|---|---|
| TC (mg/dl) | 176.4 ± 23.6 | 110.2 ± 7.9*** |
| LDL-C (mg/dl) | 94.7 ± 13.1 | 30.6 ± 14.4* |
| TAG (mg/dl) | 112.4 ± 10.2 | 65.5 ± 3.4*** |
| NEFA (mEq/L) | 0.68 ± 0.14 | 0.53 ± 0.09 |

WAT: White adipose tissue, TC: Total cholesterol, LDL-C: Low-density lipoprotein cholesterol, TAG: Triglyceride, NEFA: Non-esterified fatty acid.

As shown in Table 9, the C57BL/6J mice given saury oil in a 5% mixed feed for six weeks showed a significant decrease in blood glucose values, blood insulin concentrations, blood cholesterol, blood LDL cholesterol, and blood triglycerides.

Figure 5:
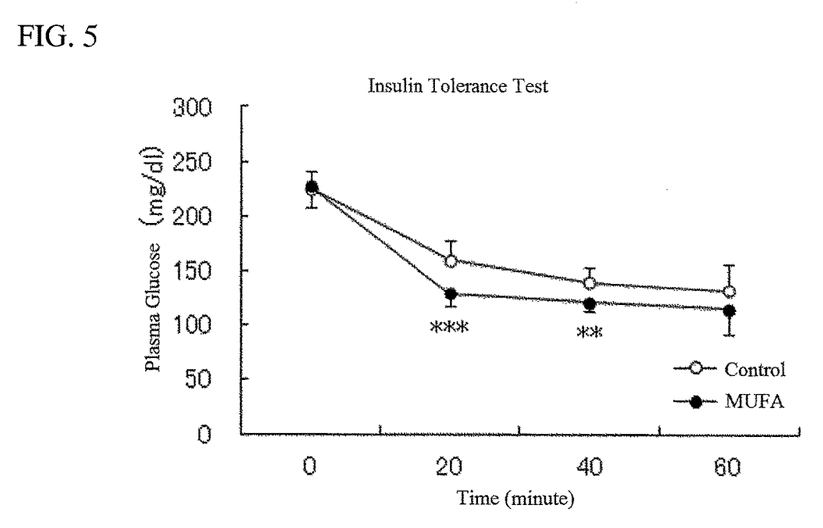
FIG. 5 is a diagram showing efficacy of MUFA-concentrated saury oil on amelioration in insulin sensitivity.

FIG. 5 is a figure showing the efficacy of MUFA-concentrated saury oil on insulin tolerance in the C57BL/6J mice. Using the C57BL/6J mice given lard in a 33% mixed feed (control group) or MUFA-concentrated saury oil in a 5% mixed feed for three weeks, an insulin tolerance test was performed. The values in the figure show an average±SE.  and * indicate a significant difference from the control group. (: $P<0.01$, *: $P<0.001$).

As shown in FIG. 5, in the insulin tolerance test, the C57BL/6J mice given MUFA-concentrated saury oil in a 5% mixed feed showed a significantly lower blood glucose value, and an ameliorative effect on insulin tolerance, compared with the C57BL/6J mice given lard in a 33% mixed feed (control group).

Figure 6:
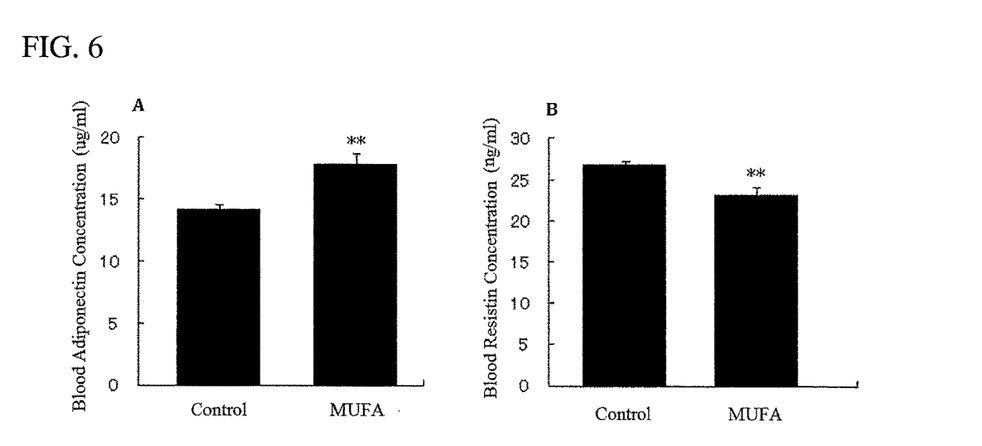
FIGS. 6A and 6B are diagrams showing efficacy of MUFA-concentrated saury oil on blood adipokine and blood resistin.

FIGS. 6A and 6B are diagrams showing the efficacy of MUFA-concentrated saury oil on plasma protein concentrations that are a benchmark for metabolic syndrome. After raising the C57BL/6J mice for a mixed feed period of six weeks, all blood were taken from mice, plasma obtained from a centrifuge was used to perform blood biochemical tests, and ELISA was used to measure the plasma adipokine levels. FIG. 6A shows the plasma adiponectin concentrations in the feed-induced obese C57BL/6J mice. FIG. 6B shows the plasma resistin concentrations in the feed-induced obese C57BL/6J mice (right). The respective values show an average ±SE (n=10). ** indicates a significant difference from the control group ($P<0.001$).

As shown in FIG. 6A, the C57BL/6J mice given the MUFA-concentrated saury oil showed a significant increase in the blood adiponectin concentrations. On the other hand, the pro-inflammatory adipocytokine resistin concentrations was significantly lower in the C57BL/6J mice given the MUFA-concentrated saury oil (FIG. 6B). It was concluded that the feed comprising MUFA-concentrated saury oil was linked to the favorable blood adipokine changes, and to the amelioration in blood glycolipid metabolism.

In the abovementioned Test 4, an ameliorative effect for metabolic syndrome was seen in the C57BL/6J mice given MUFA-concentrated saury oil with fatty acid composition as shown in Table 2. Therefore, it was shown that the efficacy of saury oil for amelioration of metabolic syndrome is not based on the EPA/DHA comprised in the saury oil, but is based on the C22:1 and C20:1 that is contained in large amounts in the saury oil.

Working Example 2

The same test as performed in Working Example 1 using saury oil was performed using Alaska pollock refined oil (deacidified, decolored). Alaska pollock oil with fatty acid composition as shown in Table 10 was mixed with feed, and the feed was fed to the feed-induced obese C57BL/6J mice. As a result of six weeks of mixed feed administration, in the same way as the results of the mixed feed administration test of saury oil for the feed-induced obese C57BL/6J mice, compared with the control lard group (lard in feed: 32%), the blood lipid (cholesterol and triglyceride) concentrations in the Alaska pollock oil group (lard in feed: 17%; Alaska pollock oil: 15%) were significantly lower (Table 11). In addition, as shown in Table 12, in comparison with the control lard group, the blood adiponectin concentrations in the Alaska pollock oil group showed a significant increase, while the blood resistin and leptin concentrations showed a significant decrease. In the same way as saury oil, the Alaska pollock oil comprising rich amounts of long-chain MUFAs showed amelioration efficacy for metabolic syndrome.

TABLE 10

| Fatty acid | (g/100 g fatty acid %) |
|---|---|
| C14:0 | 4.89 |
| C16:0 | 9.80 |
| C18:0 | 1.71 |
| C16:1 | 6.11 |
| C18:1 | 14.33 |
| C18:2 n-6 | 1.27 |
| C18:3 n-3 | 1.05 |
| C20:0 | 0.12 |
| C20:1 n-9 | 9.12 |
| C20:4 n-6 | 0.52 |
| C20:5 n-3 | 10.27 |
| C22:1 n-11 | 12.26 |
| C22:5 n-3 | 1.17 |
| C22:6 n-3 | 7.87 |

TABLE 11

| Lipids (mg/dL) | At start | Week 2 | Week 4 | Week 6 |
|---|---|---|---|---|
| | TC | | | |
| Lard group | 84.7 + 7.1 | 154.5 + 10.5 | 158.1 + 4.5 | 161.5 + 4.3 |
| Alaska pollock oil group | 80.8 + 6.0 | 112.9 + 3.7** | 130.8 + 5.7** | 113.1 + 2.7*** |
| | VLDL + IDL + LDL Cholesterol | | | |
| Lard group | 50.2 + 7.2 | 100.1 + 65.6 | 106.7 + 3.9 | 102.3 + 3.3 |
| Alaska pollock oil group | 48.2 + 6.0 | 65.64 + 3.9** | 77.1 + 6.2** | 69.4 + 2.1*** |
| | TAG | | | |
| Lard group | 56.4 + 4.4 | 80.0 + 10.1 | 95.7 + 12.9 | 118.7 + 19.8 |
| Alaska pollock oil group | 60.6 + 4.9 | 47.7 + 6.7** | 48.2 + 6.8** | 63.9 + 5.7** |

TC: Total cholesterol, VLDL: Very low density lipoprotein cholesterol, IDL: Intermediate density lipoprotein cholesterol, LDL: Low density lipoprotein cholesterol, TAG: Triglycerides.
**$P < 0.01$,
***$P < 0.001$

TABLE 12

|  | Lard group | Alaska pollock oil group |
|---|---|---|
| Adiponectin (μm/mL) | 13.8 ± 0.5 | 15.9 ± 0.5* |
| Resistin (ng/mL) | 23.7 ± 0.6 | 20.3 ± 0.9* |
| Leptin (ng/mL) | 4.1 ± 0.6 | 2.4 ± 0.5* |

*$P < 0.05$

The invention claimed is:

1. A method of raising blood adiponectin concentrations, and lessening TNF-α concentration comprising administering, to a patient in need thereof,
   an oil comprising an effective amount of at least one selected from (a) a monounsaturated fatty acid having 22 carbons, or a salt or an ester thereof, and (b) a monounsaturated fatty acid having 20 carbons, or a salt or an ester thereof,
   wherein total amount of (a) the monounsaturated fatty acid having 22 carbons, or a salt or ester thereof, and (b) the monounsaturated fatty acid having 20 carbons, or a salt or an ester thereof is at least 50% by weight of total amount of all fatty acids present in the oil.

2. The method according to claim 1, wherein the method comprises administering a glyceride of at least one selected from (a) the monounsaturated fatty acid having 22 carbons and (b) the monounsaturated fatty acid having 20 carbons.

3. The method according to claim 2, wherein the glyceride is contained in a fish oil.

4. The method according to claim 1, wherein the oil is contained in a food product.

5. The method according to claim 1, wherein the method comprises administering an effective amount of a monounsaturated fatty acid having 22 carbons or a salt or an ester thereof, wherein the monounsaturated fatty acid having 22 carbons is docosenoic acid.

6. The method according to claim 1, wherein the monounsaturated fatty acid having 20 carbons is icosenoic acid.

7. The method according to claim 1, wherein the oil comprises an ester of (a) the monounsaturated fatty acid having 22 carbons and/or (b) the monounsaturated fatty acid having 20 carbons, and the oil is derived from a fish of the family Scomberesocidae, Gadidae, Salmonidae, Osmeridae, or Clupeidae.

8. The method according to claim 7, wherein the oil is saury fish oil, or Alaska pollock oil.

9. The method according to claim 7, the oil is MUFA-concentrated.

10. The method according to claim 1, wherein the method comprises administering an oil comprising an effective amount of (a) the monounsaturated fatty acid having 22 carbons, or a salt or an ester thereof, and (b) the monounsaturated fatty acid having 20 carbons, or a salt or an ester thereof.

* * * * *